United States Patent [19]

Sugiyama

[11] 4,121,329

[45] Oct. 24, 1978

[54] IMPLEMENT FOR ATTACHING AND DETACHING BLADES FROM A BLADED TOOL

[75] Inventor: Tsuneyoshi Sugiyama, Seki, Japan

[73] Assignee: Feather Kogyo Kabushiki Kaisha, Mino, Japan

[21] Appl. No.: 767,977

[22] Filed: Feb. 11, 1977

[30] Foreign Application Priority Data

Dec. 6, 1976 [JP] Japan ................ 51-163195

[51] Int. Cl.$^2$ ............................ B25B 27/14
[52] U.S. Cl. .......................... 29/270; 81/3 R
[58] Field of Search .............. 30/1, 40.2, 90, 339, 30/322, 323; 29/270, 278; 81/3 R; 294/7

[56] References Cited

U.S. PATENT DOCUMENTS

| D. 201,291 | 6/1965 | Varkala | 30/322 X |
| 2,271,812 | 2/1942 | Clemings | 294/7 |
| 2,454,197 | 11/1948 | Muros | 30/40.2 |
| 2,801,873 | 8/1957 | Faughnder | 30/322 X |
| 2,831,379 | 4/1958 | DeFore | 81/3 R |
| 3,172,316 | 3/1965 | Grieshaber | 29/278 X |
| 3,244,317 | 4/1966 | Baybin | 30/40.2 X |
| 3,373,491 | 3/1968 | Montelius | 30/339 |
| 3,868,772 | 3/1975 | Gray | 30/90 X |

FOREIGN PATENT DOCUMENTS 517,478 10/1955 Canada ................ 30/322

Primary Examiner—Gary L. Smith

[57] ABSTRACT

An implement for attaching a blade such as a surgical knife blade to the handle of a bladed tool such as a surgical knife. The implement has a series of projections projecting outwardly from an operating edge which engage under the tip of the blade, over the middle of the blade and under the base of the blade for curving the blade. Manipulation of the blade by a handle on the implement permits the blade to be attached to or detached from a blade holding part of the tool. The implement has an L-shaped check piece on the operating edge for catching the blade if it should accidentally slip off the projections.

2 Claims, 13 Drawing Figures

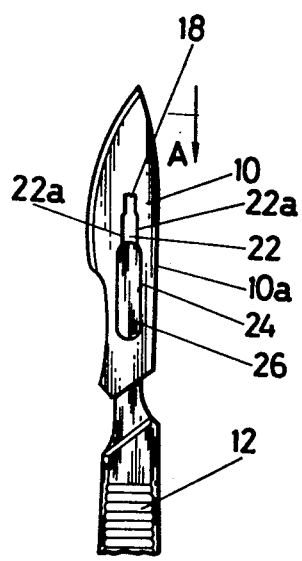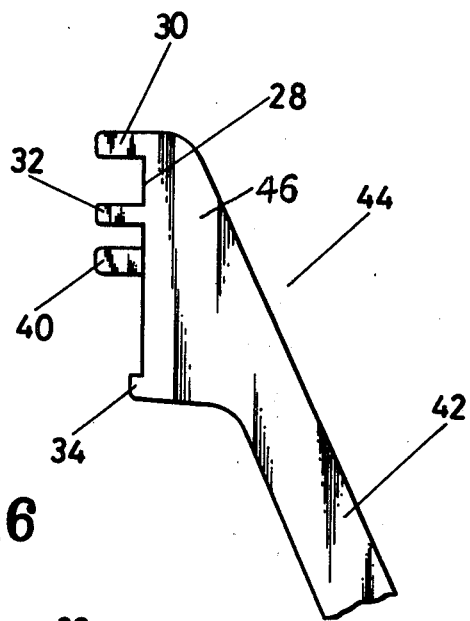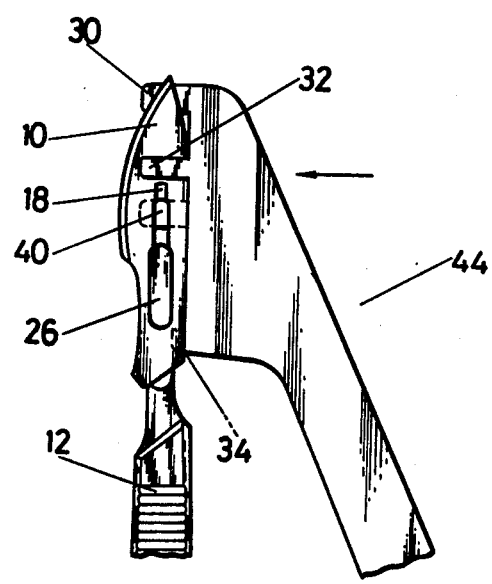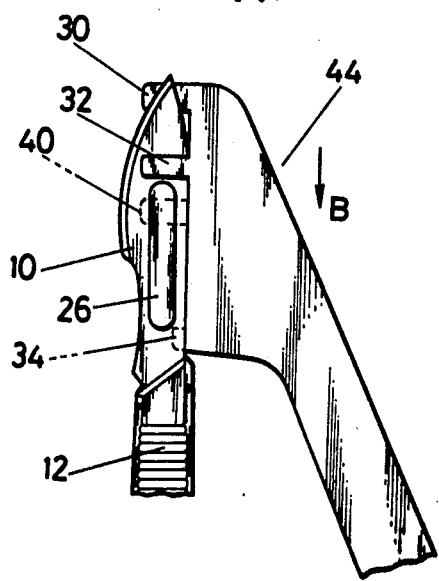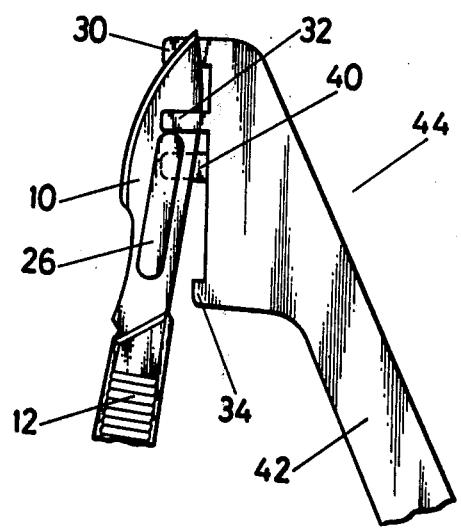

IMPLEMENT FOR ATTACHING AND DETACHING BLADES FROM A BLADED TOOL

The present invention relates to an implement for attaching a blade to and detaching a blade from a bladed tool such as a surgical knife.

Many bladed tools exist which have removable or replaceable blades. The blades are frequently snapped fitted onto the tool. Such blades are usually quite sharp, and the operation of attaching them to the tool or detaching them from the tool by hand is frequently dangerous, being likely to cause cuts to the finger of the person carrying out the attaching or detaching operation.

The object of the present invention is to provide a reliable and safe implement for attaching a blade to and detaching it from the handle of a bladed tool when it is necessary to exchange a new blade for a worn or dull blade.

Another object of the present invention is to provide such an implement which has a simple construction and a low manufacturing cost.

The invention will now be described in detail in connection with the accompanying drawings, in which:

FIGS. 4 to 8 are plan views showing the steps of attaching the blade using the implement according to the invention;

Since the implement of the present invention is for the attaching of a blade to and detaching the blade from a bladed tool having a blade and a handle of a particular construction, the construction of the said blade and the said handle will be clearly explained first.

Figure 1:
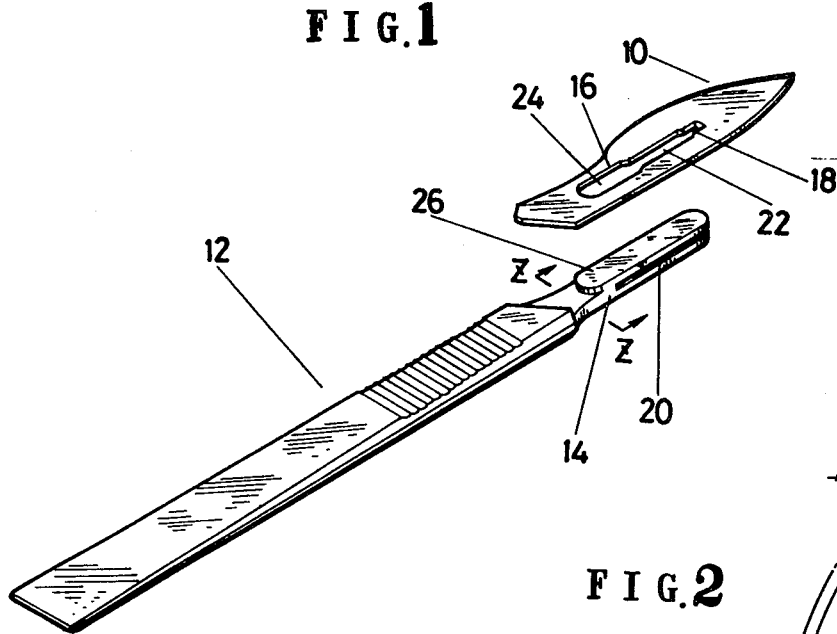
FIG. 1 is an exploded perspective view of a bladed tool, specifically a surgical knife, with which the implement of the present invention is useful.
Figure 2:
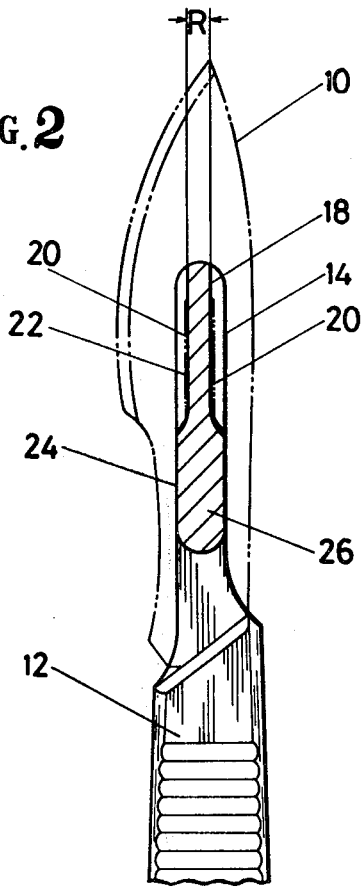
FIG. 2 is an enlarged cross-sectional view in the direction of Line Z—Z in FIG. 1 and with a blade attached to the tool handle.

The bladed tool illustrated in FIG. 1 is a surgical knife and it is composed of a handle 12 and a replacable blade 10 detachably mounted thereon. At the center of the blade 10 is a longitudinally elongated aperture 16 having three portions of different widths, namely, a large width portion 24, a medium width portion 22 and a small width portion 18 in order from the base of the tip of the blade. The blade 10 is attachable to a blade holding piece 14 which is disposed at the forward end of the said handle 12 of the knife. The width of the small width portion 18 is, as shown in FIG. 2, made coincided with a distance R between a blade receiving grooves 20 formed in opposite side edges of the blade holding piece 14 on the said handle 12. The medium width portion 22 is continuous from said small width portion 18 and has a width slightly greater than that of the said portion 18. The large width portion 24 is continuous from said portion 22 and has a width slightly greater than that of a support piece 26 which projects from one of the face surfaces of the blade holding piece 14 on the handle 12, and has the end remote from the tip of the blade of a shape complementary of the corresponding end of the support piece 26.

The handle 12 has the elongated blade holding piece 14 protruding forwardly therefrom for holding the blade 10 thereon. The support piece 26 projects slightly above one face surface of said holding piece 14 and has a width slightly less than that of the large width portion 24 of the aperture 16 in the blade 10 and, a length slightly less than the overall length of the aperture 16 in the blade 10. The blade receiving grooves 20 are disposed longitudinally in the opposite side edges of said blade holding piece 14, the distance R between the grooves 20 being equal to the width of the narrow width portion 18 of the aperture in the blade 10. Thus, when the blade 10 is attached to the blade holding piece 14, the portion of the holding piece 14 at the free end of the holding piece and between the grooves 20 is tightly engaged in the narrow width portion 18 of the aperture 16 in the blade, the portions of the blade on opposite sides of the medium width portion 22 are inserted in the blade receiving grooves 20, and the large width portion 24 of the aperture 16 is fitted tightly around the end of the support piece 26 remote from the tip of the blade.

Figure 3:
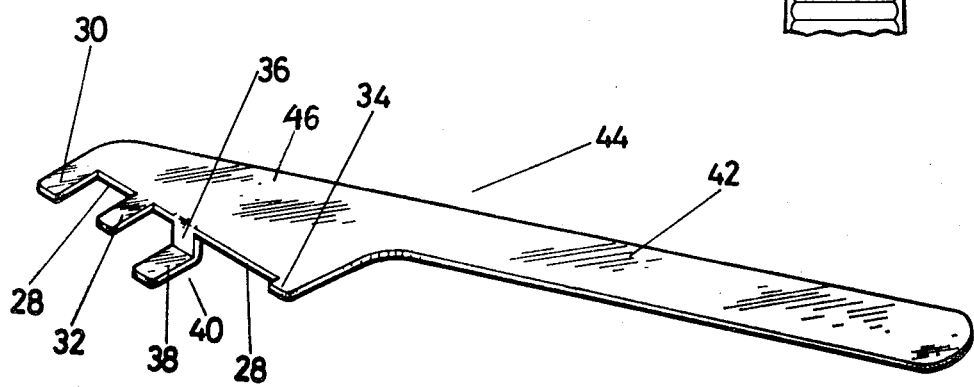
FIG. 3 is a perspective view of the implement according to the present invention.
Figure 9:
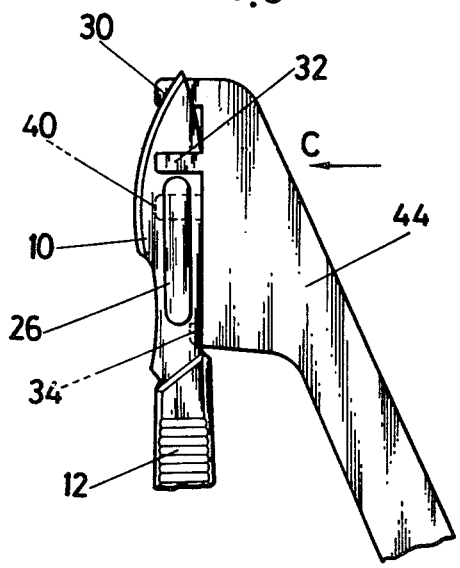
FIGS. 9 to 13 are plan views showing the steps of detaching the blade using the implement according to the invention.
Figure 10:
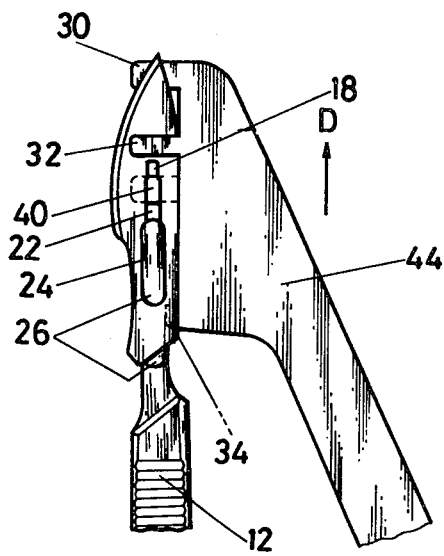
Figure 11:
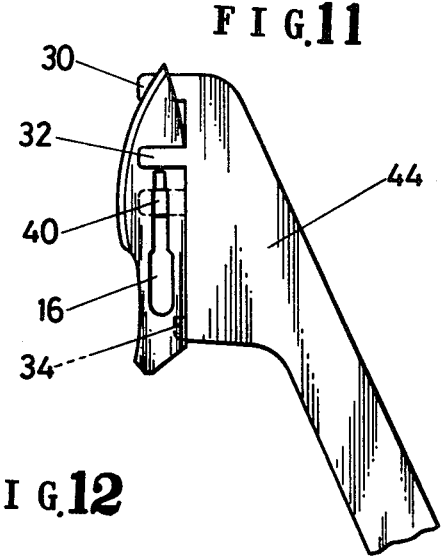
Figure 12:
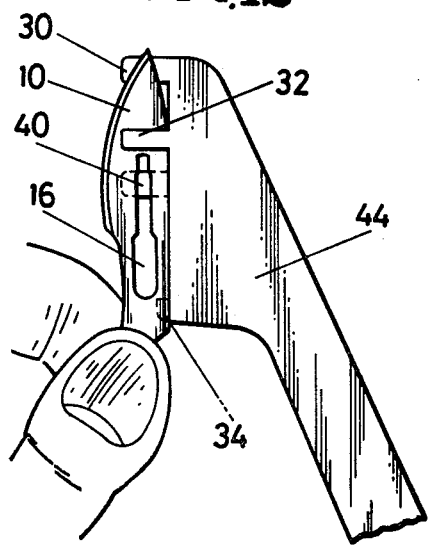
Figure 13:
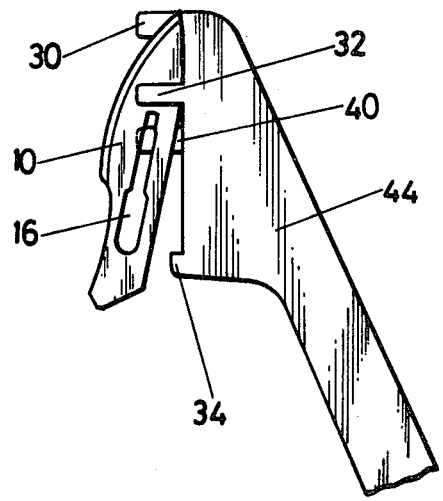

The implement 44 for attaching the blade 10 to the handle 12 and detaching the blade 10 from the handle 12 is made from a metal plate such as stainless steel or the like and is shaped as shown in FIG. 3. The body 45 of the implement has an operating edge 28 along one side thereof and a blade tip holding piece 30 at the outer end of the edge 28 and a blade holding piece 32 spaced inwardly along the edge 28 from the blade holding piece 30 project at angles to the said operating edge 28. A blade base holding piece 34 is provided at the inner end of the said operating edge 28 and projects at right angles thereto. Between the holding pieces 32 and 34 is an L-shaped check piece 40 for preventing the blade from jumping out of the implement and having a laterally projecting portion 36 projecting at a right angle to the plane of said implement and to said operating edge 28 and, a parallel projecting piece 38 extending from the free end of the laterally projecting portion parallel to the holding piece 32. A handle 42 extends from the inner end of body 46 and diverges away from said operating edge 28.

The method of using the implement of FIG. 3 to attach a blade 10 to a handle 12 is shown in FIGS. 4 to 8. With the left hand holding on the handle 12 of the bladed tool and with the right hand holding the blade 10, the enlarged width portion 14 of aperture 16 in blade 10 is placed over the holding piece 24 and the edges 22a of the medium width portion 22 of the aperture in the blade 10 are inserted into grooves 20 on both sides of the blade holding piece 14 and the blade is pushed along the holding piece 14 toward the handle 12, i.e. down as shown by the arrow A in FIG. 4. With the left hand holding the handle 12 with the blade 10 partially mounted on the blade holding piece 14, the implement 44 is held in the right hand (see FIG. 5), and the blade tip holding piece 30 is placed under the tip end of the blade 10 so as to make the back edge 10a of the blade 10 touch the operating edge 28, and the blade holding piece 32 is positioned over the blade just forward of the end of the small width portion 18 of aperture 16 in the blade 10. At this time, since the L-shaped check piece 40 projects beneath the blade 10 a distance corresponding to the length of the laterally projecting portion 36, a comparatively large space is formed between the under side of the blade 10 and the parallel projecting piece 38 for preventing the blade from jumping out of the implement. Thereupon, the handle 42 of same implement 44 is pressed with a slight force downwardly in the direction of the under side of the blade with the blade tip holding piece 30 and the blade holding piece 32 acting as fulcrums, so that the tip end of the blade 10 is bent slightly up toward the upper side thereof. Then the base holding piece 34 provided at the inner end of the operating edge 28 is placed under the under side of the blade 10 slightly beyond the end of the large width portion 24 of the aperture 16 in the blade 10 (see FIG. 6).

Thus, the tip and the base of the blade 10 are held by the blade tip holding piece 30, the blade holding piece 32 and the base holding piece 34 with the aperture 16 positioned between the projections 32 and 34. The blade is bent up toward the tip in front of the holding piece 32. With the blade held in the implement in that condition, the implement 44 is pulled along the support piece 26 toward the handle 12 as shown by the arrow B in FIG. 7. The edges 22a on both sides of the medium width portion 22 slide along the blade receiving grooves 20 on both side edges of the blade holding piece 14. The end of the large width portion 24 of the aperture 16 in blade 10 being curved upwardly from the support piece 26 as described above, the under side of the base of the blade 10 is separated slightly from the surface of the support piece 26 on the handle 12. When the movement of the implement 44 to the handle 12 is completed, the end of the large width portion 24 toward the handle 10 comes even with the corresponding end of the support piece 26. Thereupon, the handle 42 of the implement is swung away from the tool, see FIG. 8, and the projection 34 is removed from beneath the base of the blade 10, the blade 10 is restored to its original shape and the large width portion 24 of the aperture 16 in blade 10 snaps over the support piece 26. When the implement is further moved to remove the holding piece 30 and the holding piece 32 from the blade 10, the small width portion 18 toward the tip of the blade 10 will be left closely engaged with the material of the blade holding piece 14 between the blade receiving grooves 20. The attaching of the blade 10 to the handle 12 is thus complete.

The method of using the implement for detaching the blade 10 from the handle 12 is shown in FIGS. 9 to 13. With the left hand holding the handle 12 of the bladed tool to which the blade 10 is attached and, with the right hand holding on the implement 44, the said implement 44 is moved in the direction of the arrow C so as to insert the blade into holding piece 30 beneath the tip of the blade 10 and the blade holding piece 32 over the blade 10. The handle 42 of the implement 44 is then pressed toward the under side of the blade 10 with the holding pieces 30 and 32 acting as fulcrums to curve the blade, and the blade base holding piece 34 of the implement 44 is engaged with the under side of the base of the said blade 10. (see FIG. 9) With the blade 10 held in the bent shape by the holding pieces 30, 32 and 34, the large width portion 24 of the aperture 16 is first lifted upwardly over the support piece 26 by lifting the handle 42 of the implement 44 and then moving it in the direction of the arrow D in FIG. 10. After the implement 44 has been pushed in the direction of the arrow D, the small width portion 18 and the medium width portion 22 come out of the blade receiving grooves 20 and the blade 10 is then detached from the blade support piece 14. (see FIG. 11) The blade 10 is still held in the implement by the holding pieces 30, 32 and 34. In this condition the lower base part of the blade 10 is liable to come off the holding piece 34 because it is held only by a comparatively small size piece 34 and, as a result there is the possiblity of damaging clothing and injuring humans if the bowed blade 10 flys out of the implement 44 due to the resiliency of the bend blade.

The danger of the blade 10 flying away from the implement 44 if the base of the blade 10 comes off with the holding piece 34, is prevented by the L-shaped check piece 40 which is between the holding piece 34 and the holding piece 30. If the blade comes off the holding piece 34 and starts to jump away from the implement 44, it will be caught by the said check piece 40.

Finally, by holding the base of the blade 10 in the left hand and swinging the blade away from the implement, the part of the blade 10 which is supported on the holding piece 34 is removed therefrom, and the blade 10 is restored to its original flat condition so that it can be easily detached from the implement 44. (see FIGS. 12 and 13)

By the use of the implement of the present invention, a blade can be safely and securely attached to and detached from the handle of a bladed tool. Because of its simple construction, the said implement can be manufactured by punching a developed shape out of a sheet of material and bending the projecting to form the L-shaped check piece. Therefore, the manufacturing process is very simple and easy and, moreover, the manufacturing cost is low. In addition, the present invention has such a simple construction that it can be utilized readily without any real skill being required.

What is claimed is:

1. An implement for attaching a blade to and detaching the blade from a bladed tool, comprising: a flat body having an operating edge therealong; and handle extending from said body in the place of the body at an angle to said operating edge; said body having a blade tip holding piece projecting from the operating edge in the plane of the body at the other end of the operating edge from said handle, a blade holding piece projecting from the operating edge in the plane of the body at a point spaced along the operating edge from the blade tip holding piece, a blade base holding piece projecting from the operating edge in the plane of the body and at the end of the operating edge corresponding to the handle and an L-shaped check piece having one leg extending from said operating edge at a point intermediate said blade tip holding piece and said blade base holding piece and substantially perpendicular to the plane of said body and having a second leg extending from the end of the one leg in the same direction and parallel to said holding pieces.

2. An implement as claimed in claim 1 in which said L-shaped check piece is between said blade holding piece and said blade base holding piece.

* * * * *